United States Patent [19]

Nishina

[11] Patent Number: 4,944,304
[45] Date of Patent: Jul. 31, 1990

[54] ELECTRONIC SPHYGMOMANOMETER

[76] Inventor: Teruya Nishina, 4-19-403, Kita Kawara Machi, Kameoka-city, Kyoto, Japan

[21] Appl. No.: 232,040

[22] Filed: Aug. 15, 1988

[30] Foreign Application Priority Data

Aug. 14, 1987 [JP] Japan .................. 62-203282

[51] Int. Cl.$^5$ .................................. A61B 5/02
[52] U.S. Cl. ........................ 128/667; 128/687; 128/672
[58] Field of Search .................. 128/664–667, 128/632–633, 672–677, 690, 903; 356/39–41

[56] References Cited

U.S. PATENT DOCUMENTS

| | | | |
|---|---|---|---|
| 3,482,565 | 12/1969 | Gowen | 128/667 |
| 3,958,560 | 5/1976 | March | 128/633 |
| 4,677,982 | 7/1987 | Llinas et al. | 128/664 |
| 4,780,824 | 10/1988 | Niwa et al. | 128/667 X |

Primary Examiner—Angela D. Sykes
Attorney, Agent, or Firm—Wegner & Bretschneider

[57] ABSTRACT

An electric sphygmomanometer has a cuff, a pulse wave detecting photoelectric sensor including a light-emitting element and a light-receiving element which are disposed on the cuff, as well as a memory for storing measured data. Either a measuring mode or a transmitting mode may be selected, and the light-emitting and -receiving elements of the pulse wave detecting photoelectric sensor may be used as light-emitting and -receiving elements for transmission of measured data in the transmitting mode. As a result of this arrangement, it is possible to transmit measured data stored in the memory to an external data processor readily and inexpensively without the need for special hardware.

4 Claims, 3 Drawing Sheets

FIG. I

ELECTRONIC SPHYGMOMANOMETER

BACKGROUND OF THE INVENTION

1. Field of the Invention

The present invention relates to an electronic sphygmomanometer designed so that measured data which is stored in the memory can be transmitted to an external data processor by means of light communication.

2. Description of the Related Art

There has recently been proposed an electronic sphygmomanometer for finger which is provided with a pulse wave detecting photoelectric sensor designed to detect a pulse wave by a combination of light-emitting and -receiving elements.

FIG. 3 is a block diagram showing the pneumatic system and circuit configuration of the recently proposed electronic sphygmomanometer for finger.

A finger cuff 1 is defined by a cylindrical rubber bag formed such that a finger can be inserted thereinto. The finger cuff 1 has a pulse wave detecting photoelectric sensor 2 comprising a light-emitting element (light-emitting diode) 21 and a light-receiving element (phototransistor) 22 which are disposed on the inner peripheral surface of the cylindrical cuff 11. The finger cuff 11 is connected to a pressurizing motor 12 through a pneumatic tube 11. A slow exhaust valve 13, a rapid exhaust valve 14 and semi-conductor pressure sensor 15 are disposed at appropriate positions, respectively, along the pneumatic tube 11. The pressurizing motor 12 is connected to a motor driving circuit 31 which is, in turn, electrically connected to an MPU (microprocessor unit) 3 (described later), while the rapid exhaust valve 14 is connected to a rapid exhaust valve driving circuit 32, whereby the pneumatic system is driven and controlled. The semiconductor pressure sensor 15 detects the level of pressure inside the cuff 1 and outputs an analog quantity through an amplifier circuit 33. The analog quantity is converted into a digital quantity through an A/D converter 34 and this digital quantity is output to the MPU 3. It should be noted that another light-receiving element 16 for sensing a finger insertion condition is disposed at an appropriate position on the inner peripheral surface of the cuff 1.

The light-emitting element 21 of the cuff 1 projects light on the finger in response to an output command from the MPU 3, and the light-receiving element 22 detects the quantity of reflected light from the finger (i.e., the quantity of reflected light which varies in accordance with the change in volume of the artery). The quantity of reflected light is passed through a buffer amplifier 35 and the DC portion thereof is output to the MPU 3 through the A/D converter 34. The quantity of reflected light is also delivered to a filter 36 through the buffer amplifier 35. In the filter 36, the noise component (DC component) is removed and only a change in the pulse wave is taken out and amplified in an amplifier circuit 37. The amplified analog quantity is converted into a digital value in the A/D converter 34 and this digital value is output to the MPU 3.

The MPU 3 has a function of allowing the light-emitting element 21 to emit with an intensity appropriate to a subject of measurement through a D/A converter 38 and an LED driving circuit 39 and determining a highest blood pressure value and a lowest blood pressure value using a predetermined algorithm on the basis of the pulse wave amplitude of the pulse wave signal taken in from the light-receiving element 22 and the cuff pressure. The MPU 3 also has a function of storing the results of measurement (i.e., the determined blood pressure values) in a memory incorporated therein and digitally displaying the measured values on a display (LCD) 43.

To the MPU 3 are further electrically connected a power supply circuit 41 provided with a power supply switch 40 and a measurement start switch 42.

One type of the above-described electronic sphygmomanometer for finger is designed so that blood pressure values measured on a plurality of occasions, that is, past data, can be stored in the memory of the MPU for a predetermined period of time (e.g., one month). This measured data storage type electronic sphygmomanometer is considerably effective in diagnostically examining a change in the patient's condition since it is possible for an expert such as a doctor to make a diagnosis on the basis of a plurality of measured data (blood pressure values) obtained for a predetermined period of time which are transmittted from the electronic sphygmomanometer to an external special-purpose data processor (installed in a hospital or the like).

However, in order to transmit measured data obtained on a plurality of occasions and stored in the MPU (memory) from the conventional electronic sphygmomanometer to an external special-purpose data processor with a display unit which is installed in a hospital or the like, it is necessary to attach an interface to the MPU, connect together the instrument body and the special-purpose data processor through a connecting cable, and transmit measured data through this transmission line. Accordingly, there is a need for extra hardware arrrangements such as an interface, output buffer, connector, etc. for transmitting the measured data stored in the memory. Thus, the prior art suffers from the disadvantages that the overall size of the electronic sphygmomanometer increases and the cost of the instrument rises.

SUMMARY OF THE INVENTION

In view of the above-described circumstances, it is a primary object of the present invention to provide an electronic sphygmomanometer which is designed so that measured data stored in the memory can be transmitted to an external data processor readily and inexpensively without the need for a special hardware arrangement.

To this end, the present invention provides an electronic sphygmomanometer having a cuff, a pulse wave detecting photoelectric sensor including a light-emitting element and a light-receiving element which are disposed on the cuff, and memory means for storing measured data, wherein the improvement comprises: mode selecting means for selecting either a measuring mode or a transmitting mode; and means for allowing the light-emitting and -receiving elements of the pulse wave detecting photoelectric sensor to be used as light-emitting and -receiving elements for transmission of measured data in the transmitting mode.

By virtue of the above-described arrangement, in the measuring mode, measurement of blood pressure is executed and measured blood pressure values are displayed on a display (LCD). In addition, the measured data (blood pressure values) are stored in the memory of the MPU. When pieces of measured data which were obtained on a plurality of occasions are to be transmitted to an external data processor installed, for example, in a hospital so that a doctor makes a diagnosis on the basis of the measured data, transmission means which is connected to the external data processor is fitted into the cuff of the sphygmomanometer. In this state, the light-emitting and -receiving elements of the transmission means face the pulse wave detecting photoelectric sensor (i.e., the light-receiving and -transmitting elements for the measuring mode) provided in the cuff. If, in this state, a transmitting mode switch which is provided on the instrument body is turned ON, the photoelectric element (light-emitting element) for measurement is allowed to be used as an optical element for tranmission of measured data. In other words, the blood pressure measuring mode is changed to the measured data transmitting mode. Then, the MPU reads measured data stored in the memory and outputs digital signals representing the measured data to the optical element (light-emitting element) for transmission to thereby flash the light-emitting element. This light (flashing signal) is received by the light-receiving element of the transmission means connected to the external data processor and the measured data is thereby transmitted to the circuit section of the external data processor.

It should be noted that the measuring mode may be automatically changed to the transmitting mode by the operation of the MPU. More specifically, the arrangement may be such that the external data processor causes the light-emitting element of the transmission means to emit light and this light is received by the light-receiving element provided on the cuff to request the MPU to change over the operating mode from the measuring mode to the transmitting mode. In this case, the transmitting mode switch is unneccesary.

BRIEF DESCRIPTION OF THE DRAWINGS

The above and other objects, features and advantages of the present invention will become more apparent from the following description of the preferred embodiment thereof, taken in conjunction with the accompanying drawings, in which like reference numerals denote like members, and of which.

DESCRIPTION OF THE PREFERRED EMBODIMENT

The present invention will be described hereinunder in more detail with reference to FIGS. 1 and 2.

Figure 1:
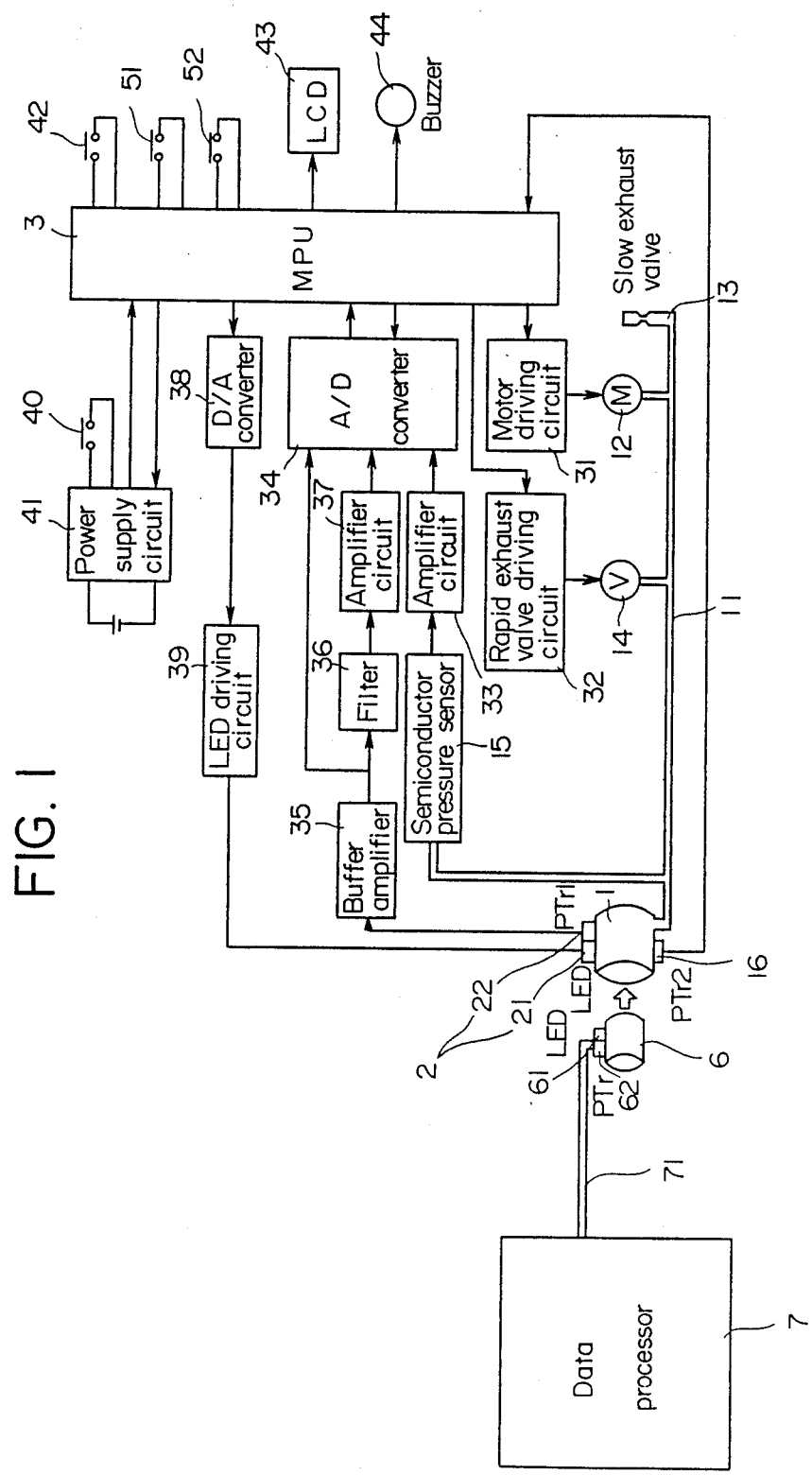
FIG. 1 is a block diagram showing the pneumatic system and circuit configuration of one embodiment of the electronic sphygmomanometer according to the present invention.
Figure 2:
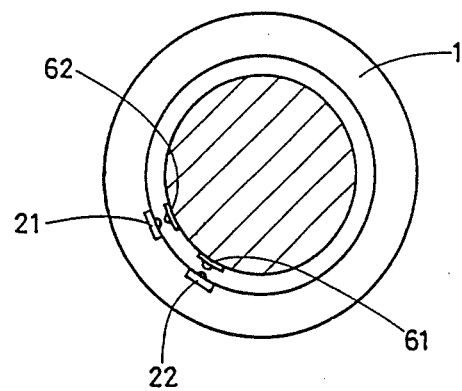
FIG. 2 is a sectional view showing the cuff having transmission means fitted thereinto.
Figure 3:
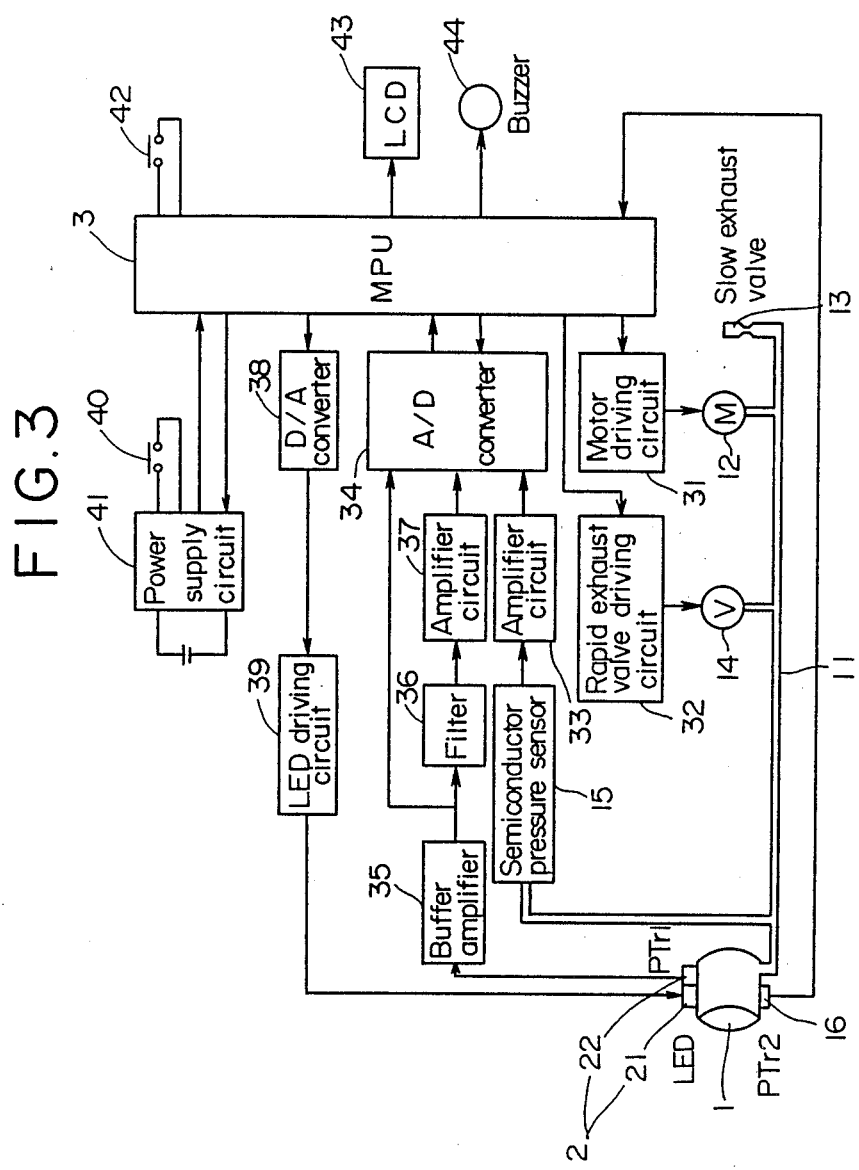
FIG. 3 is a block diagram showing the pneumatic system and circuit configuration of a conventional electronic sphygmomanometer.

FIG. 1 is a block diagram showing the pnuematic system and circuit configuration of one embodiment of the electronic sphygmomanometer according to the present invention.

The electronic sphygmomanometer comprises an instrument body having an electronic circuit section and a finger cuff 1 which is connected to a pressurizing motor 12 provided on the instrument body through a pneumatic tube 11 and which has a pulse wave detecting photoelectric sensor 2. An external data processor 7 is provided with transmission means 6 which is detachably fitted into the finger cuff 1. The transmission means 6 has light-emitting and -receiving elements 61 and 62 for transmission which correspond to the light-emitting and -receiving elements 21 and 22, respectively, provided on the cuff 1 to transmit measured data to the circuit section of the external data processor 7 by means of light communication.

The finger cuff 1 is defined by a cylindrical rubber bag formed such that a finger can be inserted thereinto. The finger cuff 1 has a pulse wave detecting photoelectric sensor 2 comprising a light-emitting element (light-emitting diode) 21 and a light-receiving element (phototransistor) 22 which are disposed on the inner peripheral surface of the cylindrical cuff 11. The finger cuff 11 is connected to a pressurizing motor 12 through a pneumatic tube 11. A slow exhaust valve 13, a rapid exhaust valve 14 and a semi-conductor pressure sensor 15 are disposed at appropriate positions, respectively, along the pneumatic tube 11. The pressurizing motor 12 is connected to a motor driving circuit 31 which is, in turn, electrically connected to an MPU (microprocessor unit) 3 (described later), while the rapid exhaust valve 14 is connected to a rapid exhaust valve driving circuit 32, whereby the pneumatic system is driven and controlled. The semiconductor pressure sensor 15 detects the level of pressure inside the cuff 1 and outputs an analog quantity through an amplifier circuit 33. The analog quantity is converted into a digital quantity through an A/D converter 34 and this digital quantity is output to the MPU 3. It should be noted that another light-receiving element 16 for sensing a finger insertion condition is disposed at an appropriate position on the inner peripheral surface of the cuff 1.

The light-emitting element 21 of the cuff 1 projects light on the finger in response to an output command from the MPU 3, and the light-receiving element 22 detects the quantity of reflected light from the finger (i.e., the quantity of reflected light which varies in accordance with the change in volume of the artery). The quantity of reflected light is passed through a buffer amplifier 35 and the DC portion thereof is output to the MPU 3 through the A/D converter 34. The quantity of reflected light is also delivered to a filter 36 through the buffer amplifier 35. In the filter 36, the noise component (DC component) is removed and only a change in the pulse wave is taken out and amplified in an amplifier circuit 37. The amplified analog quantity is converted into a digital value in the A/D converter 34 and this digital value is output to the MPU 3.

The MPU 3 has a function of extracting a pulse wave amplitude from the pulse wave signal input thereto and determining a highest blood pressure value and a lowest blood pressure value using a predetermined algorithm on the basis of the pulse wave amplitude and the cuff pressure and also has a function of storing the determined blood pressure values as measured data in a RAM (memory) incorporated therein. Further, the MPU 3 has a function of adjusting the reflectivity which depends on each individual subject's finger. More specifically, the MPU 3 reads the reflectivity (refraction level) of the subject from the DC component (the DC level carrying the pulse wave) which is taken in directly from the buffer amplifier 35 and controls the D/A converter 38 and the LED driving circuit 39 such that the light-emitting element 21 emits light with a controlled intensity.

To the MPU 3 are further electrically connected a power supply circuit 41 provided with a power supply switch 40 and a measurement start switch 42, together with an LCD (Liquid Crystal Display) 43 for displaying results of measurement (blood pressure values) and a buzzer 44 for urging the operator to perform various operations.

The feature of the present invention resides in that the MPU 3 is provided with a function of selecting either a measuring mode or a transmitting mode and the measured data stored in the memory is transmitted from the light-emitting and -receiving elements 21 and 22 to the transmission means 6 of the external data processor 7 by means of light communication in the transmitting mode.

In this embodiment, the mode selecting function of the MPU 3 is exemplarily realized as follows. A measuring mode switch 51 and transmitting mode switch 52 are connected to the MPU 3, and when the transmitting mode switch 52 is turned ON, the measuring mode is changed to the transmitting mode and the measuring element for detection of a pulse wave, that is, the light-emitting element 21, is switched to an optical element 21 for transmission of measured data (i.e., the light-emitting element 21 for measurement is used as the light-emitting element 21 for transmission). On the other hand, the transmission means 6 is a columnar member which is fitted into the cylindrical cuff 1. The transmission means 6 has a light-emitting element (light-emitting diode) 61 for transmission and a light-receiving element (phototransistor) 62 for transmission which are disposed at appropriate positions, respectively, on the peripheral surface thereof so that, when the transmission means 6 is fitted into the cuff 1, the light-emitting and -receiving elements 61 and 62 for transmission face the light-receiving and -emitting elements 22 and 21, respectively, of the cuff 1 (see FIG. 2). The transmission means (light-emitting and -receiving elements 61 and 62) 6 is connected to the circuit section of the external data processor 7 through a cable 71. Transmission of measured data from the MPU 3 to the optical element (light-emitting element) 21 for transmission of the cuff 1 is executed by substitutionally using the control circuit for controlling the intensity of the light emitted from the light-emitting element 21, that is, the combination of the D/A converter 38 and the LED driving circuit 39. For example, the measured data stored in the memory of the MPU 3 is output in the form of digital signals to the D/A converter 38, and the LED driving circuit 39 drives the light-emitting element 21 with a level corresponding to the logic state of each of the bits constituting a code corresponding to each of the digital signals. More specifically, the light-emitting element 21 is flashed in accordance with codes corresponding to the measured data (signals). Thus, the light-emitting element 21 outputs optical code signals.

In the electronic sphygmomanometer having the above-described arrangement, when measurement of blood pressure is to be effected, the measuring mode switch 51 is turned ON to select the measuring mode. When measured data (blood pressure values) obtained in the past and stored in the memory is to be transmitted to the external data processor 7, the transmission means (columnar member) 6 is fitted into the cuff 1. In this state, the light-emitting and -receiving elements 61 and 62 of the transmission means 6 face the light-receiving and -emitting elements 22 and 21, respectively, of the cuff 1 (see FIG. 2). Then, the transmitting mode switch 52 is pressed. In consequence, the light-emitting element 21 which is used to detect a pulse wave in the measuring mode is substituted for an optical element for transmission of measured data. In other words, the measuring mode is changed to the transmitting mode. Then, the MPU 3 reads the measured data stored in the memory and outputs the data signal to the D/A converter 38 which, in turn, outputs an analog signal to the LED driving circuit 39. Thus, the light-emitting element 21 is flashed to transmit the measured data signal in the form of an optical signal. The light-receiving element 62 for transmission receives the signal and transmits it to the external data processor 7.

It should be noted that, although in the embodiment the measuring mode switch 51 and the transmitting mode switch 52 are provided in order to change the measuring mode to the transmitting mode, the measuring mode switch 51 may be omitted, that is, the arrangement may be such that the normal state of the instrument is defined as the measuring mode and the measuring mode is changed to the transmitting mode by actuating the transmitting mode switch 52.

Although in the embodiment the measurng mode switch 51 and the transmitting mode switch 52 are provided on the electronic sphygmomanometer, the mode selecting arrangement is not necessarily limited thereto. For example, the arrangement may be such that a transmission request signal is sent to the MPU 3 from the external data processor 7 through the light-emitting element 61 for transmission and the light-receiving element 22 and the MPU 3 automatically changes over the operating mode from the measuring mode to the transmitting mode in response to the request signal. In this case, it is unnecessary to provide not only the measuring mode switch 51 but also the transmitting mode switch 52.

Thus, according to the present invention, the pulse wave detecting photoelectric element is allowed to be used as an optical element for transmission and reception of measured data by changing over the operating mode from the measuring mode to the transmitting mode. Therefore, if the transmission means having light-emitting and -receiving elements for transmission is fitted into the cuff, measured data can be transmitted from the optical element for transmission to an external data processor through the light-receiving element for transmission by means of light communication. Thus, it is possible to transmit measured data to an external data processor readily and inexpensively.

Accordingly, it becomes unnecessary to provide hardware arrangements such as an interface, output buffer, connector, etc. for transmitting measured data to an external data processor (special-purpose processor) as in the case of the conventional electronic sphygmomanometer. Therefore, no extra parts such as a connector or other attachments are exposed to the outside of the instrument body. Thus, it is possible to obtain excellent product design and further reduce the size and weight of the instrument.

Although the present invention has been described through specific terms, it should be noted here that the described embodiment is not necessarily exclusive and various changes and modifications may be imparted thereto without departing from the scope of the invention which is limited solely by the appended claim.

What is claimed is:

1. An electronic sphygmomanometer comprising a cuff, a pulse wave detecting photoelectronic sensor comprising a light-emitting element and a light-receiving element which are disposed on said cuff, memory means for storing measured data, mode selecting means for selecting either a measuring mode or a transmitting mode; and means for allowing the light-emitting and -receiving elements of said pulse wave detecting photoelectric sensor to be used as light-emitting and -receiving elements for tranmission of measured data in said transmitting mode.

2. The electronic sphygmomanometer of claim 1, wherein the means for allowing the light-emitting and -receiving elements to be used for transmission of measured data in the transmitting mode comprises a member associated with the cuff to which the light-emitting and -receiving elements are connected and means connecting said member to an external data processor.

3. The electronic sphygmomanometer of claim 1, wherein the mode selecting means comprises means for transmitting a transmission request signal from an external data processor through the light-emitting element to the memory means, whereby the memory means automatically changes from the measuring mode to the transmitting mode in response to the transmission request signal.

4. The electronic sphygmomanometer of claim 1, wherein the member is in the form of a column.

* * * * *